(12) United States Patent
Lopez

(10) Patent No.: US 11,609,223 B2
(45) Date of Patent: Mar. 21, 2023

(54) DEVICE AND A METHOD FOR ANALYSIS OF CELLS

(71) Applicant: IMEC VZW, Leuven (BE)

(72) Inventor: Carolina Mora Lopez, Leuven (BE)

(73) Assignee: IMEC VZW, Leuven (BE)

( * ) Notice: Subject to any disclaimer, the term of this patent is extended or adjusted under 35 U.S.C. 154(b) by 672 days.

(21) Appl. No.: 16/035,574

(22) Filed: Jul. 13, 2018

(65) Prior Publication Data

US 2020/0018742 A1  Jan. 16, 2020

(51) Int. Cl.
| | |
|---|---|
| G01N 33/483 | (2006.01) |
| G01N 27/414 | (2006.01) |
| H03F 3/45 | (2006.01) |
| B01L 3/00 | (2006.01) |
| B01J 19/00 | (2006.01) |

(52) U.S. Cl.
CPC ..... *G01N 33/4836* (2013.01); *G01N 27/4145* (2013.01); *B01J 19/0093* (2013.01); *B01J 2219/00653* (2013.01); *B01L 3/5085* (2013.01); *B01L 2200/0647* (2013.01); *B01L 2300/0819* (2013.01); *H03F 3/45188* (2013.01)

(58) Field of Classification Search
CPC ............ G01N 33/4836; G01N 27/4145; B01J 19/0093; B01J 2219/00653; B01L 3/5085; B01L 2200/0647; B01L 2300/0819; H03F 3/45188
See application file for complete search history.

(56) References Cited

FOREIGN PATENT DOCUMENTS

EP    1965210 B1    12/2012

OTHER PUBLICATIONS

Dragas, Jelena, et al. "In vitro multi-functional microelectrode array featuring 59 760 electrodes, 2048 electrophysiology channels, stimulation, impedance measurement, and neurotransmitter detection channels." IEEE journal of solid-state circuits 52.6 (2017): 1576-1590. (Year: 2017).*

Lopez, Carolina Mora, et al. "An implantable 455-active-electrode 52-channel CMOS neural probe." IEEE Journal of Solid-State Circuits 49.1 (2013): 248-261. (Year: 2013).*

(Continued)

*Primary Examiner* — Robert J Eom
(74) *Attorney, Agent, or Firm* — Moser Taboada

(57) ABSTRACT

A device for analysis of cells comprises: an active sensor area (104) presenting a surface for cell growth; a microelectrode array (102) comprising a plurality of pixels (110) in the active sensor area (104), wherein each pixel (110) comprises at least one electrode (120) at the surface, wherein each pixel (110) is configured to control the configuration of the pixel circuitry and set a measurement modality of the pixel; recording circuitry having a plurality of recording channels (130), wherein each pixel (110) is connected to a recording channel (130), wherein each recording channel (130) comprises a reconfigurable component (131), which is selectively controlled between being set to a first mode, in which the reconfigurable component (131) is configured to amplify a received pixel signal, and being set to a second mode, in which the reconfigurable component (131) is configured to selectively pass a frequency band of the received pixel signal.

16 Claims, 12 Drawing Sheets

(56) References Cited

OTHER PUBLICATIONS

Gao, Cencen, et al. "An ultra-low-power extended counting ADC for large scale sensor arrays." 2014 IEEE international symposium on circuits and systems (ISCAS). IEEE, 2014. (Year: 2014).*

Chi et al., "A Multi-Modality CMOS Sensor Array for Cell-Based Assay and Drug Screening", IEEE Transactions on Biomedical Circuitsand Systems, vol. 9, No. 6, Dec. 2015, pp. 801-814.

Tsai et al., "High-channel-count, high-density microelectrode array for closed-loop investigation of neuronal networks", Conference Proceedings of IEEE Engineering in Medicine and Biology Society, 2015, pp. 7510-7513.

Park et al., "A High-Density CMOS Multi-Modality Joint Sensor/Stimulator Array with 1024 Pixels for Holistic Real-Time Cellular Characterization", 2016 IEEE Symposium on VLSI Circuits, Honolulu, Hawaii, USA, Jun. 15-17, 2016.

Dragas et al., "In Vitro Multi-Functional Microelectrode Array Featuring 59 760 Electrodes, 2048 Electrophysiology Channels, Stimulation, Impedance Measurement, and Neurotransmitter Detection Channels", IEEE Journal of Solid-State Circuits, vol. 52, No. 6, Jun. 2017, pp. 1576-1590.

* cited by examiner

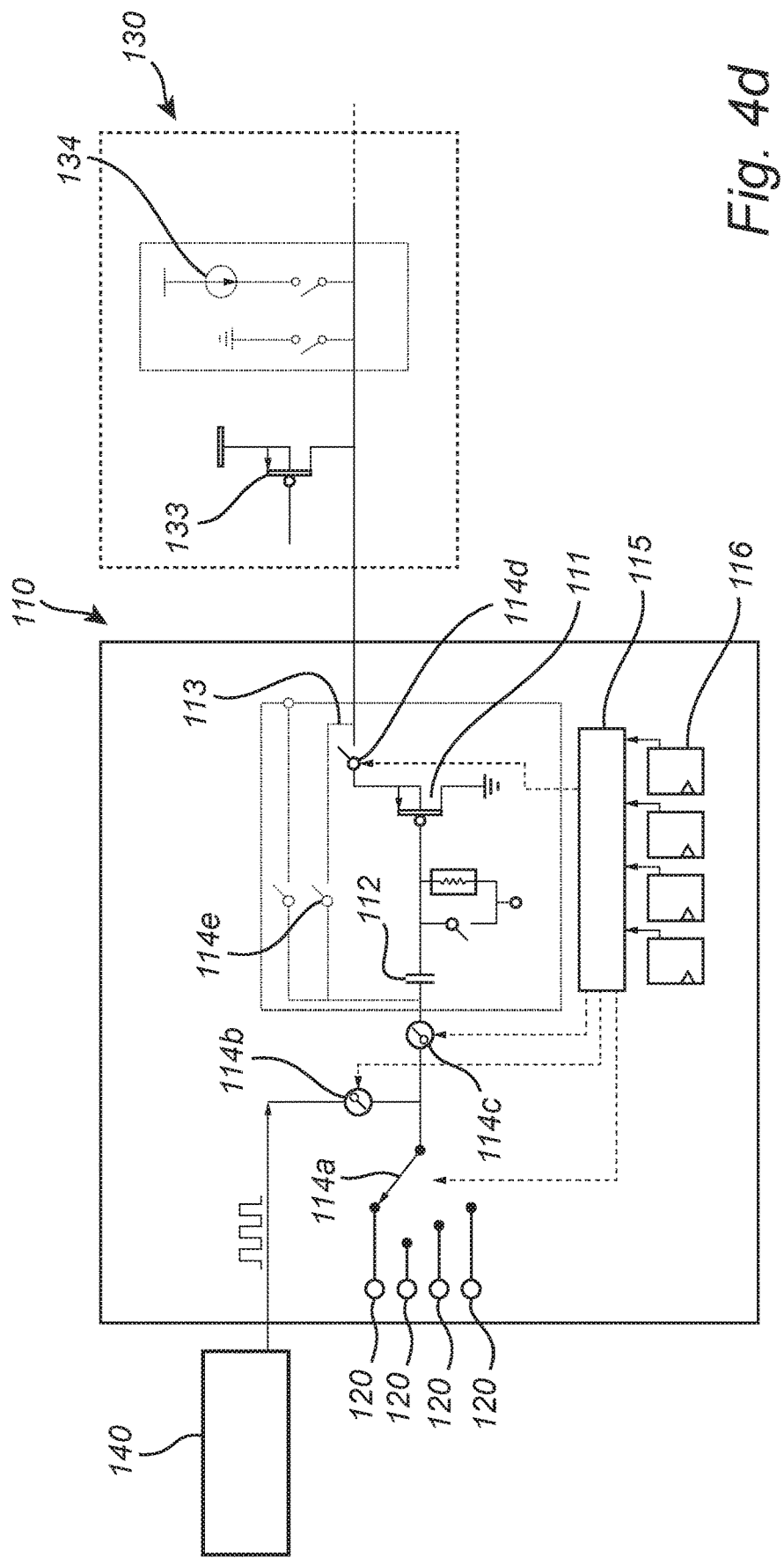

DEVICE AND A METHOD FOR ANALYSIS OF CELLS

TECHNICAL FIELD

The present inventive concept relates to a device for analysis of cells and a method for manufacturing of such a device. In particular, the present inventive concept relates to a device wherein cells are cultured in vitro on a surface of the device.

BACKGROUND

Studying of cell behavior may be of interest in many cell-physiological and medical applications. In order to study cell behavior, cells are typically cultured in vitro.

The cultured cells may be analyzed in order to study cell behavior. For instance, it may be of interest to perform electrical sensing in order to detect electrical signals in the cultured cells. It may be of interest to detect different electrical characteristics of the cultured cells.

A device for analysis of cells may be provided with a microelectrode array, wherein circuitry is arranged in an active sensor area, on which cells are grown. Thus, the circuitry of the microelectrode array may form contact with the cells for detecting electrical characteristics of the cells.

However, it may be very difficult to perform detection of different electrical characteristics of a single cell within the cultured cells. Detection of different electrical characteristics may require different circuitry for performing the detection, which implies that the circuitry for different analyses may not access the same cell or that a relatively large distance is required between two adjacent pixels in the microelectrode array for performing detections.

Further, signals detected by electrodes of the microelectrode array may need to be processed in different manners in order to extract different characteristics of the cells. Each type of processing of the signals may require dedicated circuitry, which implies that the microelectrode array may need to be combined with a very large circuitry area (not necessarily coinciding with the active sensor area) for performing processing of signals. Although a size of such signal processing circuitry may not affect a spatial resolution with which analysis of cells may be made, a large size may still affect a compactness of the device as a whole and a price of the device as dependent on an integrated circuit area.

Therefore, it would be desired to have an improved flexibility of circuitry for performing analyses of cultured cells and especially for performing a plurality of modalities of analyses.

SUMMARY

An objective of the present inventive concept is to enable improved analysis of cells and, in particular, for sensing of electrical signals of cells in a dense arrangement of sensing electrodes and while requiring a small area of circuitry for signal processing.

This and other objectives of the present inventive concept are at least partly met by the invention as defined in the independent claims. Preferred embodiments are set out in the dependent claims.

According to a first aspect, there is provided a device for analysis of cells, said device comprising: an active sensor area presenting a surface for cell growth on the device; a microelectrode array comprising a plurality of pixels in the active sensor area, wherein each pixel comprises at least one electrode at the surface, wherein the at least one electrode is configured to form contact with cells for providing stimulating signals to cells and/or measuring electrical signals from cells, wherein each pixel further comprises pixel circuitry comprising at least one switch for setting a configuration of the pixel circuitry and wherein each pixel is configured to individually receive a control signal for controlling the configuration of the pixel circuitry and set a measurement modality of the pixel; recording circuitry having a plurality of recording channels, wherein each pixel is connected to a recording channel, the recording channel being configured to receive signals from the pixels in the active sensor area, and wherein each recording channel of the recording circuitry comprises a reconfigurable component, which is selectively controlled between being set to a first mode, in which the reconfigurable component is configured to amplify a received pixel signal, and being set to a second mode, in which the reconfigurable component is configured to selectively pass a frequency band of the received pixel signal.

According to the invention, the device comprises a reconfigurable component, which may be controlled to selectively amplify a received pixel signal or pass a frequency band of the received pixel signal. Thus, the same reconfigurable component may be used in various different sensor modalities such that the same recording circuitry may be used for processing signals from the pixels for each sensor modality.

In the first mode, the reconfigurable component may comprise a differential amplifier, which may be configured to receive the pixel signal and a reference signal for amplifying and detecting the pixel signal.

In the second mode, the reconfigurable component may comprise a differential amplifier, which is set to selectively activate a modulating element for modulating the received pixel signal and control a frequency band of the received signal that is passed by the reconfigurable component. This may be used in order to ensure that impedance spectroscopy measurements may be properly performed, wherein an impedance is determined at a (varying) frequency used for stimulating a cell and the received signal is processed to remove lower frequency signals corresponding to e.g. intracellular action potentials or extracellular action potentials.

A gain of the reconfigurable component and/or the recording circuitry may also be set in dependence of the signal to be detected, which may differ for different sensor modalities.

Thanks to the pixel circuitry comprising a switch for setting a configuration of the pixel circuitry, the same pixel circuitry may be used for different analyses in dependence on the received control signal. Thus, the signal for different measurement modalities may be acquired from the same pixel and provided to the same recording channel, wherein the recording channel is further set, through at least a control of the reconfigurable component, to appropriately process the received signal.

The recording circuitry may receive a pixel signal, which is acquired from an electrode among at least one electrode. The pixel may comprise a plurality of electrodes, such that e.g. an electrode in the pixel closest to the cell may be chosen.

The recording circuitry may further receive a reference signal, such that a differential signal may be detected. The reference signal may be received from a dedicated reference pixel comprising one or more reference electrodes. The reference pixels may be shared, such that the pixel signal of plural recording pixels may be processed in relation to the same reference signals.

As used herein, the term "pixel" should be construed as an addressable element, which may be used for acquiring a signal for detecting one or more characteristics of a cell. The plurality of pixels may thus form information in two dimensions corresponding to cells associated with each spatial position of a pixel in the array. The information in two dimensions is thus based on the signals acquired from individual pixels and could be used to e.g. form an image as a representation of detected or determined characteristics in the two spatial dimensions. However, the pixel should not be construed as necessarily determining an intensity of light, but rather the pixels determine electrical signals relating to cells, which may be converted to information about the cells.

The recording channel may be configured to receive signals from the pixels in the active sensor area, which implies that the recording channel does not need to be arranged within the active sensor area. This implies that integrated circuit area required for forming circuitry of the recording channel need not be arranged in the active sensor area on which cells are cultured and hence a size of an area of the recording circuitry need not affect a spatial resolution with which information of cultured cells may be acquired.

According to an embodiment, the reconfigurable component in the second mode is configured to receive a modulation signal which is synchronized with an input current for stimulating cells on the active sensor area, wherein the reconfigurable component is configured to modulate the received pixel signal with the modulation signal for downconversion of the received pixel signal to baseband.

A stimulating signal may be used for enabling measurement of an impedance of the cells. In particular, it may be interesting to determine the impedance for a plurality of different frequencies of the stimulating signal. However, in order to correctly determine the impedance, the impedance signal may be separated by the reconfigurable component from lower frequency components in the received pixel signal, such as recording of intracellular action potential or extracellular action potential.

Thanks to the possibility to configure the reconfigurable component in the second mode to downconvert the received pixel signal to baseband, the reconfigurable component may be used for facilitating detection of the impedance.

According to an embodiment, the reconfigurable component in the first mode is configured to inactivate a modulating element and to amplify the received pixel signal.

Thus, by the modulating element being selectively inactivated, the reconfigurable component may function as a differential amplifier for detecting signals in sensor modalities when no stimulating signal is provided. The reconfigurable component may then in the first mode e.g. be able to amplify intercellular action potential signals or extracellular action potential signals.

According to an embodiment, the pixel is configured to be set to a recording mode, wherein a signal from the at least one electrode is connected to a source follower, which is further connected to a recording channel of the recording circuitry for providing a pixel signal to the recording channel.

The pixel may thus in a recording mode be connected to a source follower, which may store a voltage signal detected by the electrode for read-out of the signal. The pixel may thus be selectively set into a configuration where a signal may be read out from the pixel to the recording channel. This may facilitate use of the pixel not only for detection of signals.

The electrode may be AC-coupled to the source follower in order to remove offset and low-frequency drifts of electrode potential.

According to an embodiment, the pixel is configured to be set to a stimulation mode, wherein the at least one electrode is connected to receive a stimulating signal.

Thus, pixel may be set to be configured both in a stimulation mode and in a recording mode, such that the pixels may be used both for providing stimulating signals to cells and recording signals from cells. This implies that a compact circuitry may be associated with a cell, such that the microelectrode array may enable dense sensing of signals from cells while also allowing sensing of signals based on stimulating signals provided to cells.

The stimulating signal may be used in detecting of an impedance of the cell, wherein a signal induced by the stimulating signal may be detected so as to determine the impedance.

According to an embodiment, the pixel is configured to be set to the stimulation mode followed by a recording mode, wherein a signal from the at least one electrode is connected to a source follower, which is further connected to a recording channel of the recording circuitry for providing a pixel signal to the recording channel, such that the signal detected by the at least one electrode in the recording mode corresponds to an intracellular action potential.

The stimulating signal may be used to achieve localized electroporation, which may facilitate low impedance recording of the intracellular action potential of the cell. The same pixel may thus be used to first cause electroporation by setting the pixel in the stimulation mode and then to detect the intracellular action potential by setting the pixel in the recording mode.

However, it should be realized that intracellular action potential may alternatively be detected by setting a first pixel in the stimulation mode for providing a stimulating signal to cause electroporation and simultaneously setting a second pixel in the recording mode for detecting the intracellular action potential.

According to an embodiment, the pixel comprises a plurality of electrodes and the pixel is configured to be set to an impedance measurement mode, wherein at least a first electrode is configured to be connected to receive a stimulating signal and at least a second electrode is configured to be connected to a source follower, which is further connected to a recording channel of the recording circuitry for providing a pixel signal to the recording channel.

The pixel may thus provide a stimulating signal for determining a signal response based on the stimulating signal, which implies that an impedance may be determined. At least a first electrode may be used for providing the stimulating signal, whereas at least a second electrode may be used for recording the signal induced by the stimulating signal. This implies that a tetrapolar setup for impedance measurement may be used, wherein stimulating and recording electrodes are separate. However, it should be realized that the same electrodes may be used for stimulating and recording, such that a bipolar recording of the impedance is performed, wherein e.g. a stimulation current is provided and an induced voltage is detected.

According to an embodiment, the recording channel comprises a current source, which is configured to provide a current with a fixed, pre-set frequency, and wherein the pixel in the impedance measurement mode is configured to be connected to receive a signal from the current source for receiving the stimulating signal.

This may be used for very fast recording of an impedance for a selected frequency. The device may thus enable the current source to provide the stimulating signal when an impedance measurement for the pre-set frequency is desired in a fast manner. There is no need of providing settings for controlling the frequency of the signal to be provided to the pixel, which implies that the impedance measurement may be performed based on a single control activating the current source of the recording channel.

The current source may provide a current signal such that the impedance measurement may then be performed based on a detected voltage induced by the stimulating current signal in a bipolar impedance recording setup.

The current source may be set for providing a single pre-set frequency. However, according to an alternative, the current source may be set to selectively provide a current signal having one of a few, pre-set frequencies, such as enabling fast impedance detection in e.g. two different frequencies.

The use of the impedance measurement with the current source of the recording channel may e.g. facilitate fast monitoring of impedance changes.

According to an embodiment, the device further comprises a stimulation unit for controlling generation of the stimulating signal, wherein the pixel in the impedance measurement mode is configured to be connected to the stimulation unit for receiving the stimulating signal, wherein the stimulation unit is configured to sweep a frequency of the stimulating signal for performing impedance spectroscopy measurements.

Thus, the device may comprise the stimulation unit for generating stimulating signals, such that the device includes components for both generating and providing stimulating signals to cells and for recording signals from the cells. This implies that a self-contained device may be provided, which does not need to be combined with external or further devices for enabling detecting signals for analysis of cells.

The stimulation unit may be configured to sweep a frequency, which implies that impedance may be measured over a range of frequencies swept by the stimulation unit. Thus, impedance spectroscopy may be performed using the device.

In an embodiment, the stimulation unit may be configured to sweep the frequency in a range of 10 Hz-1 MHz. This may be a suitable range for performing impedance spectroscopy. However, it should be realized that other ranges may equally be provided depending on the frequency range in which analysis is desired.

According to an embodiment, the stimulation unit comprises a current-steering architecture with independent source and sink outputs for generating output of two different current levels.

The impedance measured during impedance spectroscopy may range from tens of G$\Omega$ to hundreds of k$\Omega$, i.e. differ by five orders of magnitude. Thus, the stimulation unit may need to be able to generate vastly different current levels, typically spanning from few pA to hundreds of nA. By using a binary current-steering architecture with independent source and sink outputs, the different current levels may be achieved.

The current-steering architecture may include a reference generating unit, which is able to selectively generate two different current references, which may be used by the current-steering architecture for controlling the output current level. The reference generating unit may combine a current splitter and a current generator for generating the two different current references.

According to an embodiment, the stimulation unit comprises a charge balancing unit for preventing residual charge injection from electrode to cell.

Thus, the charge balancing unit may ensure that residual charge is not injected into electrode-cell interface so as not to affect measurements performed on the cells.

According to an embodiment, the device further comprises a digital control unit being configured to provide control signals for controlling configuration of the pixels and of the reconfigurable components of the recording channels.

The digital control unit may be configured to control functionality of the device. Thus, the control signals provided by the digital control unit may set an operation mode of the device.

The device may further comprise a human interface for allowing an operator to control functionality of the device by providing input to the digital control unit.

According to an embodiment, each recording channel further comprises a signal conditioning unit, which is configured to receive a signal from the reconfigurable component and process the signal.

Thus, the recording channel may further process the received signal to adapt the received signal to analysis to be made. For instance, the signal conditioning unit may be configured to filter the signal and/or amplify the signal.

Filtering or amplification (or any other processing) of the signal may be selectively activated depending on the signal analysis to be made. For instance, the signal conditioning unit may selectively pass the signal through at least one filter, such as a high-pass filter and/or a low-pass filter. Further, the signal conditioning unit may selectively pass the signal through an amplifier, such as a programmable gain amplifier, which may selectively set the gain of the amplifier depending on the signal being detected.

According to a second aspect, there is provided a method for analysis of cells which are arranged on an active sensor area of a microelectrode array comprising a plurality of pixels, wherein each pixel comprises at least one electrode forming contact with a cell and each pixel is connected to a recording channel, the recording channel being configured to receive signals from the pixels and having a reconfigurable component, said method comprising: providing a pixel control signal for setting a configuration of the pixel circuitry to select a measurement modality of the pixel; providing a recording channel control signal for setting a configuration of the reconfigurable component to select a mode of processing a received signal from the pixel, acquiring a measurement signal by the pixel based on the selected measurement modality and transferring a pixel signal to the recording channel; and processing the received pixel signal by the recording channel based on the selected mode of processing.

Effects and features of this second aspect are largely analogous to those described above in connection with the first aspect. Embodiments mentioned in relation to the first aspect are largely compatible with the second aspect.

Thanks to the method, the same recording channel may be used for processing different signals from pixels, such that a small integrated circuit area for providing signal processing may be used while enabling multiple measurement modalities.

BRIEF DESCRIPTION OF THE DRAWINGS

The above, as well as additional objects, features and advantages of the present inventive concept, will be better understood through the following illustrative and non-limiting detailed description, with reference to the appended drawings. In the drawings like reference numerals will be used for like elements unless stated otherwise.

FIGS. 4a-d are schematic views illustrating different configurations of the pixel circuitry of FIG. 3.

DETAILED DESCRIPTION

Analysis of cell electrophysiology may be of interest in many different applications. Study of cell electrophysiology may be particularly useful in preclinical drug discovery in order to determine how cells would react when treated by a drug to be tested.

In order to improve speed of analysis of cells, multielectrode arrays (MEAs) have been introduced, which may provide a high throughput, especially for in vitro measurements of extracellular (ExC) action potentials (APs). However, ExC measurements may not be sufficient to fully study drug toxicity.

Thus, it is also of interest to enable detection of intracellular (InC) APs. Access to InC APs within a cell for reliable detection of InC voltage may be achieved by highly-localized electroporation. The electroporation of cells may thus allow low-impedance electrical recording of the InC voltage.

In addition, impedance measurement may also be used to study cells, such as for study of cell morphology, adhesion, differentiation and contractility. Impedance measurement may include impedance spectroscopy, wherein the impedance of a cell is determined for a plurality of frequencies in a range of frequencies. ExC/InC recording and impedance measurements may also be complementary for determining drug toxicity.

Figure 1:
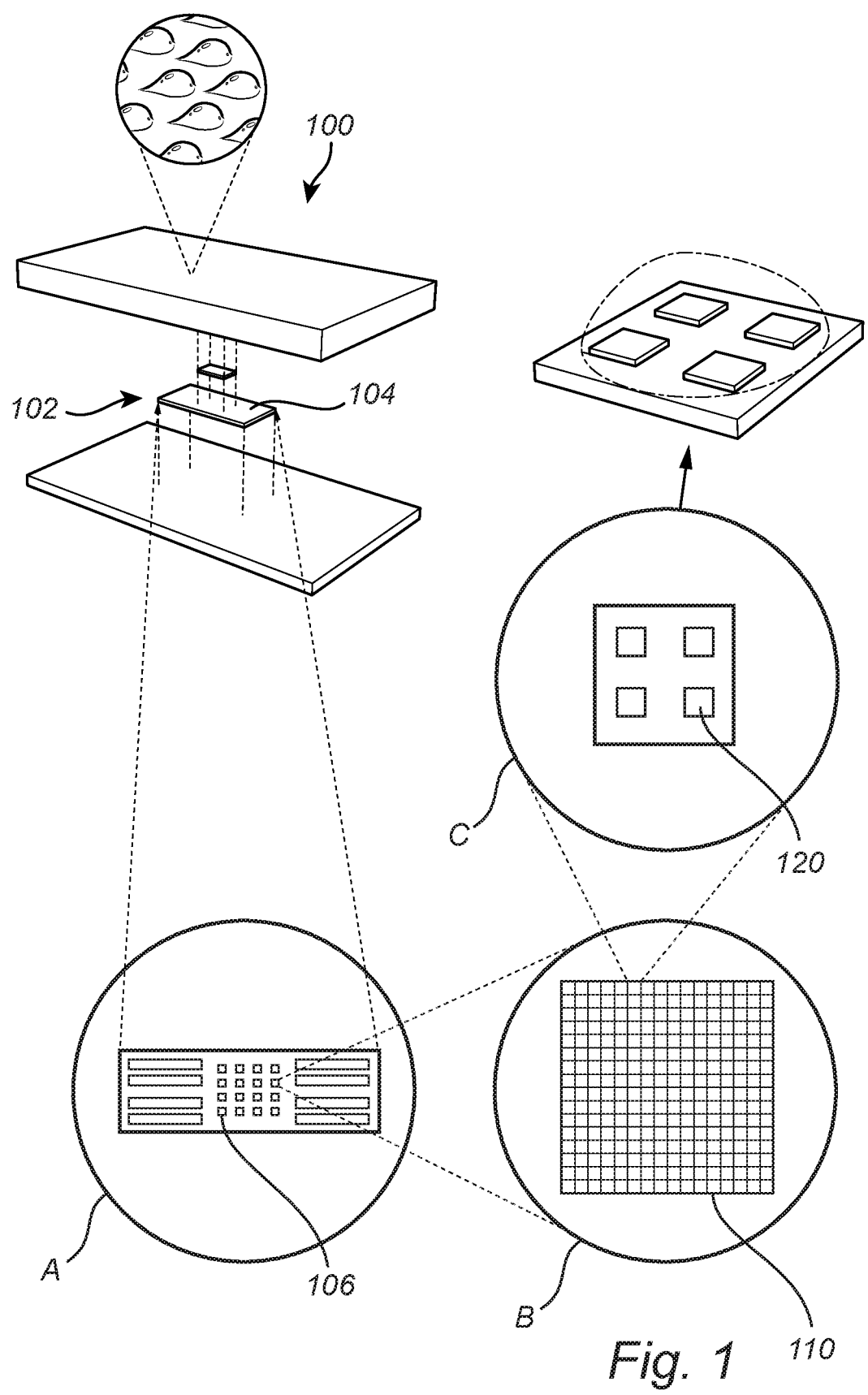
FIG. 1 is a schematic view of a device according to an embodiment.

Referring now to FIG. 1, a device 100 comprising a MEA 102 according to an embodiment will be described. The MEA 102 may be implemented by forming electric circuitry of the MEA with complementary metal-oxide-semiconductor (CMOS) technology. This may facilitate mass production of the device 100 including the MEA 102.

The device 100 comprises an active sensor area 104. The active sensor area 104 may comprise a surface on which cells may be arranged or cultured. The active sensor area 104 may have a plurality of wells in which different cells or differently treated cells may be arranged so as to enable analysis of several different factors using the same MEA 102.

The device 100 is configured to enable multiple measurement modalities. As indicated in magnifications A, B and C, the device 100 may comprise a plurality of wells 106, see magnification A, which may each comprise a plurality of pixels 110, see magnification B, which may further comprise a plurality of electrodes 120 for enabling selection of an active electrode 120 in the pixel 110. The pixels 110 may further be connected to a plurality of recording channels 130 (see FIG. 2). The device 100 may enable setting configurations of pixels 110 and recording channels 130 such that the same pixels 110 may be used for a plurality of measurement modalities.

Some pixels 110 may be configured such as to be able to be set in a plurality of different configurations to enable use of the pixel 110 in any of the measurement modalities, whereas other pixels 110 may be configured for a dedicated measurement.

Thus, the MEA 102 may comprise a plurality of configurable pixels 110, but may also comprise other pixels 110 which are pre-set for a single use.

The pixels 110 may be configured to set in one or more of the following measurement modalities:

1) ExC recording, wherein a potential outside a cell may be measured. This may be used to determine an action potential rate, which may be used for studying e.g. drug induced arrhythmia.

2) InC recording, wherein a potential within a cell may be measured. This may be used to determine a shape of the AP, which may be used for studying details of the shape of the AP, such as AP duration, slope and amplitude.

3) Constant voltage stimulation (CVS) for controlled electrode potential. This may be used to influence cell behavior, which may then be studied or to induce electroporation for InC recording.

4) Constant current stimulation (CCS) for controlled charge delivery. This may be used to influence cell behavior, which may then be studied or to induce electroporation for InC recording.

5) Fast impedance monitoring (IM) at a fixed frequency. This may be used to detect an impedance of the cell, which may be useful in determining or monitoring cell contractility.

6) Impedance Spectroscopy (IS) in a frequency range of 10 Hz-1 MHz. This may be used to detect an impedance of the cell as a function of frequency and may be useful in studying cell morphology and adhesion or for differentiating between different cells, e.g. based on cell-membrane impedance.

The pixels 110 may be configured such that different measurement modalities are simultaneously used for different pixels 110. Alternatively, the different measurement modalities may be sequentially used.

The device 100 may be configured with multi-well assays in a single chip, such that the six modalities can be used independently and simultaneously in different cell assays.

Figure 2:
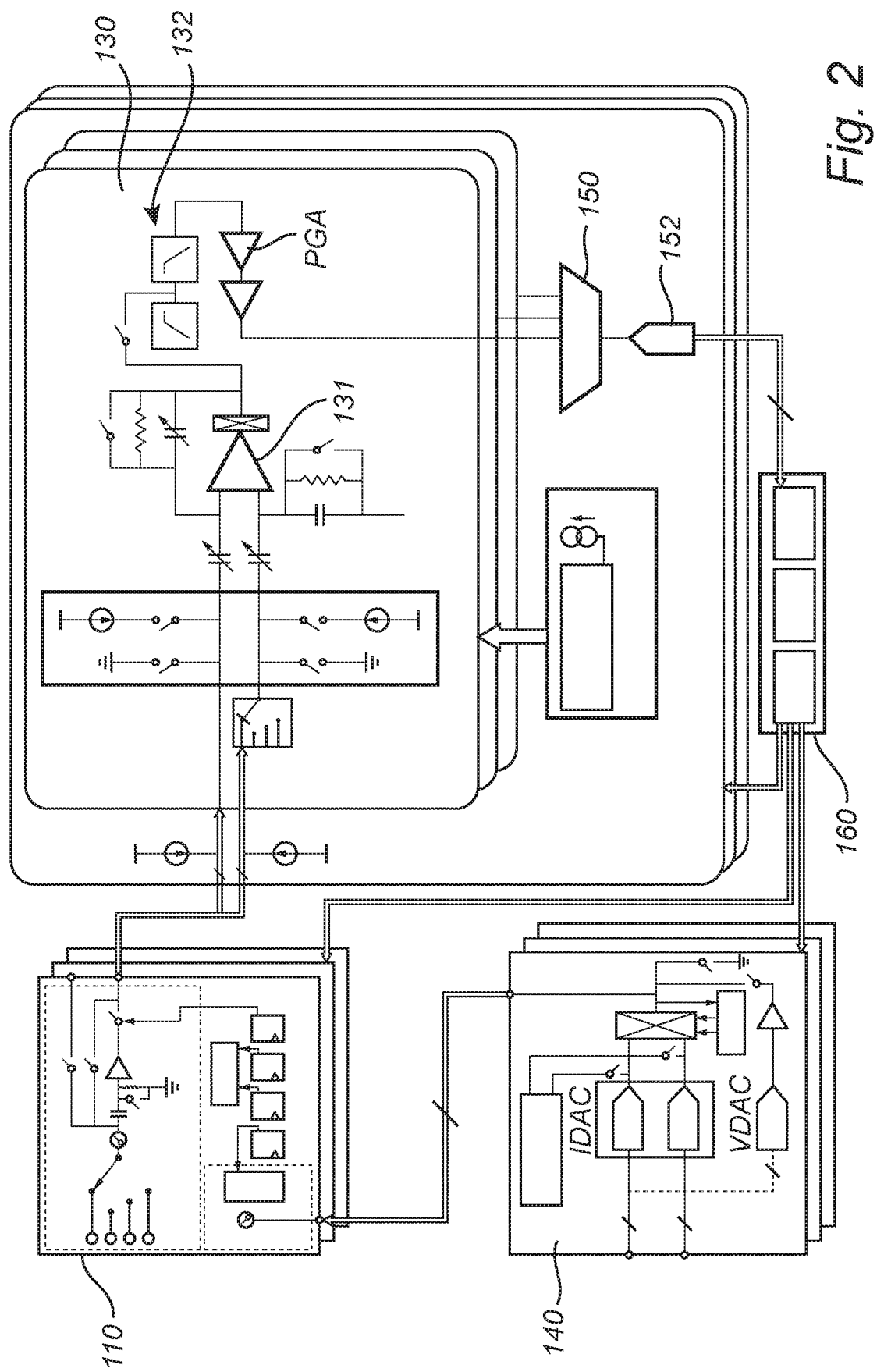
FIG. 2 is a schematic view of circuitry of the device.

Referring now to FIG. 2, the device circuitry for implementing the MEA 102 with pixels 110 and the recording channels 130 will be further described.

As illustrated in FIG. 2, the MEA 102 comprises a plurality of pixels 110. The pixels 110 may be differently configured depending on measurement modality to be used, as will be described in further detail below.

The device 100 further comprises a plurality of recording channels 130. The device 100 may be provided with one recording channel 130 per pixel 110, such that a pixel 110 is statically connected to one recording channel 130. However, it should be realized that some pixels 110 may only be used for stimulation of cells, e.g. for providing a controlled electrode potential to the pixel 110, such that no recording channel 130 needs to be associated with such pixels 110.

The device 100 further comprises a plurality of stimulation units 140 for generating stimulating signals and providing the stimulating signals to pixels 110. The device 100 may comprise a single stimulation unit 140 supporting all of the pixels 110. However, in order to enable the stimulation unit 140 to handle the load of the plurality of pixels 110, a plurality of stimulation units 140 is preferably used.

The recording channel 130 may be set in different configurations depending on the measurement modality. The recording channel 130 may comprise a reconfigurable component 131, which may be set to process a received pixel signal based on a set configuration, as will be further described below.

The recording channel 130 may further comprise a signal conditioning unit 132, which receives a signal from the reconfigurable component 131 and may further process the signal. The signal conditioning unit 132 may comprise a high-pass filter and a low-pass filter, which may each be selectively active and which may also be controlled to change a cut-off frequency of the filters. The signal conditioning unit 132 may further comprise an amplifier, which may be selectively active to amplify the possibly filtered signal. The amplifier may be implemented as a programmable gain amplifier, such that a gain of the amplifier may be controlled.

The recording channels 130 may be arranged into groups, which may further share circuitry components. Thus, the device 100 may further comprise one or more multiplexers 150 and an analog-to-digital converter (ADC) 152 associated with each multiplexer 150. Thus, outputs from the recording channels 130 may be time-multiplexed and digitized using shared ADCs.

The device 100 may further comprise a digital control unit 160. The digital control unit 160 may be configured to generate control signals for controlling the pixels 110, recording channels 130 and stimulation units 140. The digital control unit 160 may thus selectively activate and set configurations of the pixels 110, recording channels 130 and stimulation units 140. The digital control unit 160 may comprise an interface through which control signals may be transmitted. In an embodiment, the interface is a universal asynchronous receiver/transmitter (UART) interface.

The digital control unit 160 may further be configured to receive digitized outputs from the recording channels 130 from the ADCs 152.

The digital control unit 160 may be configured to process the digitized outputs for performing analysis of the cells. However, the digital control unit 160 may alternatively comprise a transmitter for transmitting measurement results to an external unit, in which further analysis of the results may be performed.

The digital control unit 160 may comprise a memory, which may store configurations to be used by the device 100 and may also store executable programs which may be run by the digital control unit 160 for controlling functionality of the digital control unit 160.

The digital control unit 160 may also use the memory or a separate memory for, at least temporarily, storing measurement results before transmitting the results to an external unit or for enabling analysis of the stored measurement results.

The digital control unit 160 may also comprise an interface for enabling the digital control unit 160 to be controlled by an operator. The digital control unit 160 may directly receive input from such an interface, e.g. a keyboard or an interactive screen, or the device 100 may comprise a dedicated unit handling a human interface, which may convert input via the human interface to appropriate control signals or messages to be transmitted to the digital control unit 160.

The digital control unit 160 may be implemented in hardware or as any combination of software and hardware. For instance, the digital control unit 160 may comprise a central processing unit (CPU) comprising software for providing functionality of the digital control unit 160 in a general-purpose processor. Alternatively, the digital control unit 160 may be implemented as firmware arranged in an embedded system on the device 100. As a further alternative, the digital control unit 160 may be implemented as a special-purpose circuitry for providing specific logical operations. Thus, the digital control unit 160 may be provided in the form of an application-specific integrated circuit (ASIC), an application-specific instruction-set processor (ASIP) or a field-programmable gate array (FPGA).

Figure 3:
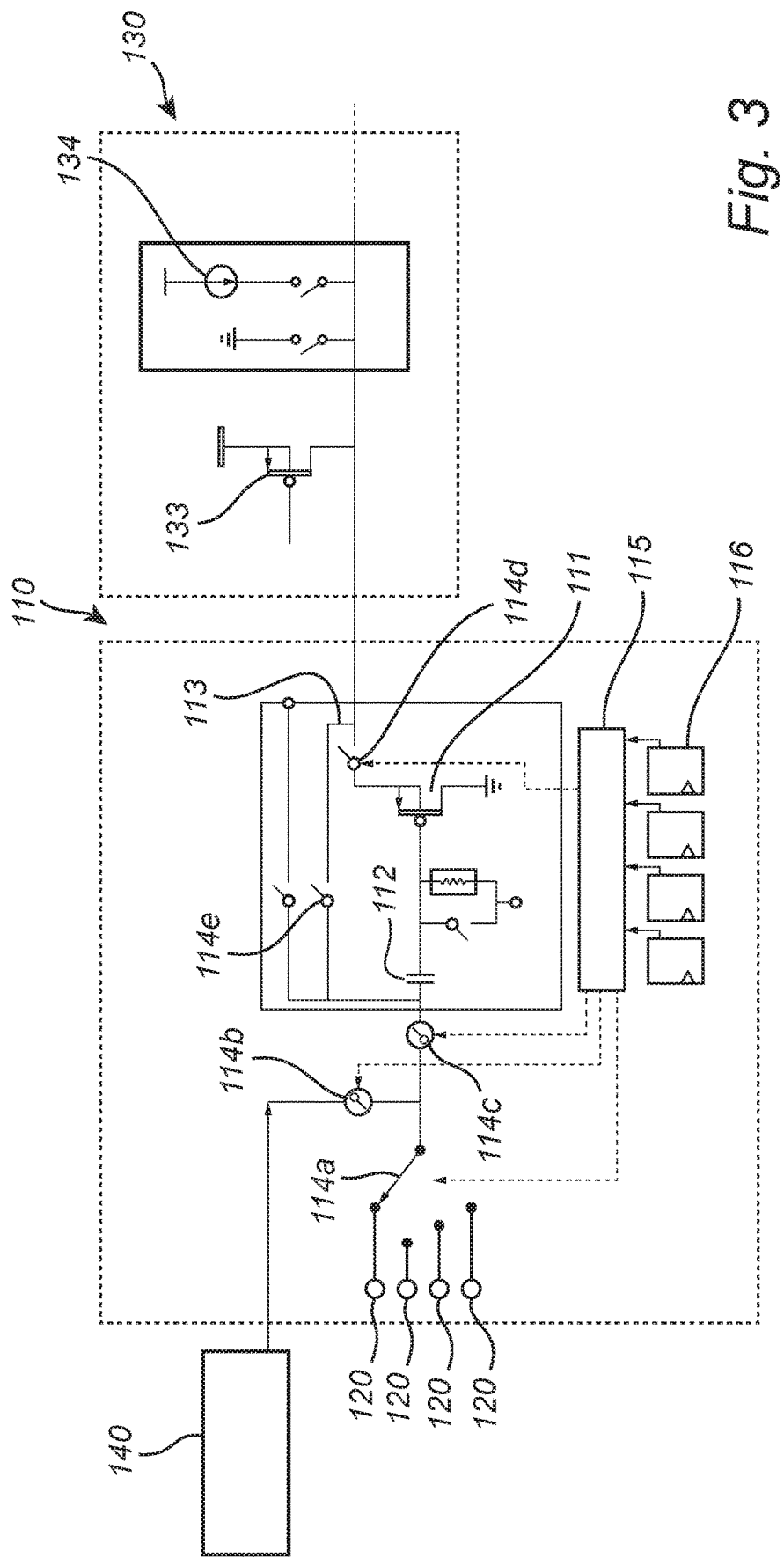
FIG. 3 is a schematic view of pixel circuitry of the device.

Referring now to FIG. 3, a pixel 110 will be further described. The pixel 110 may comprise a plurality of electrodes 120, which may form contact with cells.

The pixel 110 may further be connected to one of the stimulation units 140 such that a stimulating signal may be received by the pixel 110 from the stimulation unit 140. The stimulating signal may be connected to one of the electrodes 120 for providing a stimulating signal to a cell in contact with the electrode 120.

The pixel 110 may further comprise a source follower 111. The source follower 111 may store a voltage signal detected by the electrode 120 to enable the voltage signal to be read out from the pixel 110. The source follower 111 may thus further be connected to a recording channel 130.

The source follower 111 may be AC-coupled to the electrode 120 via a capacitor 112. This may ensure that offset in the signal from the electrode 120 and that low-frequency drifts of electrode potential are removed.

The pixel 110 further comprises a direct connection 113 between the electrodes 120 and the recording channel 130. Thus, the electrodes 120 may be connected directly to the recording channel 130 by-passing the source follower 111.

The pixel 110 may comprise a plurality of switches 114, which may be used in setting a configuration of the pixel circuitry. The pixel 110 may thus further comprise logic 115, which may control the switches 114. The logic 115 may be configured to receive a control signal for controlling the configuration of the pixel circuitry. The pixel 110 may further comprise a memory 116, which may store the configuration settings of the pixel 110.

The switches 114 may include a first switch 114a, which may be used for selecting which electrode 120 of the pixel 110 that is to be active. The selection of an active electrode 120 via the switch 114a may be performed independently of other configuration settings of the pixel circuitry, such that any of the electrodes 120 may be active for any of the configurations of the pixel circuitry.

FIG. 3 also illustrates components of the recording channel 130 facilitating read-out of signals from the pixel 110. Thus, the recording channel 130 may comprise a selector 133, which comprises a transistor which may be selectively activated for providing a bias current to the source follower 111 for activating read-out of a signal from the pixel 110.

The recording channel 130 may further comprise a current source 134, which is configured to provide a current with a fixed, pre-set frequency to the pixel 110. The current source 134 may be selectively activated for providing a stimulating signal to the pixel 110. The current source 134 may be able to provide a plurality of different frequencies, such that the current source 134 may select one pre-set frequency from a group of at least two available pre-set frequencies.

Referring now to FIGS. 4a-d, different configurations of the pixel 110 will be described.

Figure 4A:
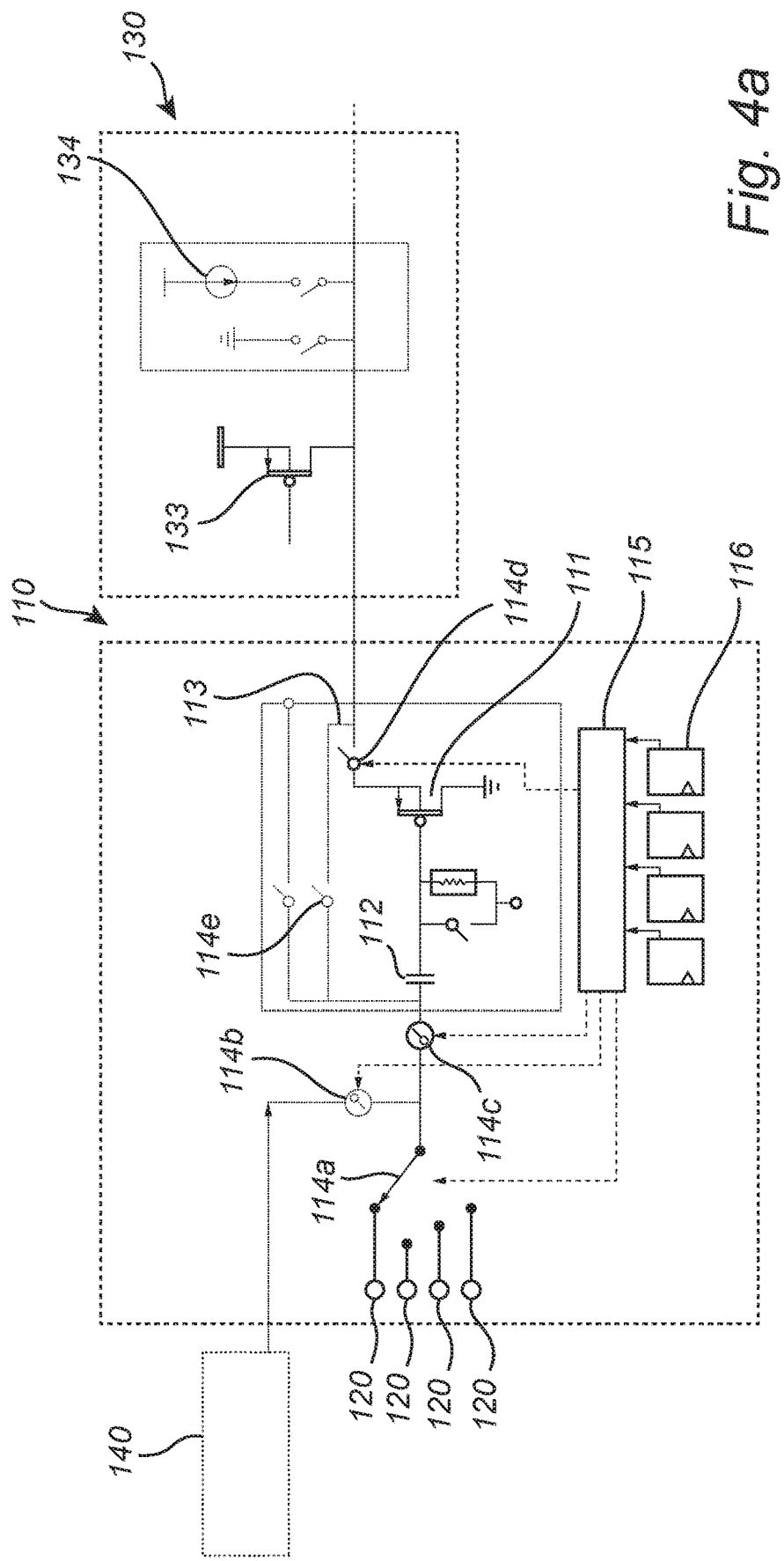

In FIG. 4a, configuration settings for the pixel 110 in a recording mode is illustrated. Here, a second switch 114b is not active, which implies that the pixel 110 is not connected to the stimulation unit 140. Further, a third switch 114c and a fourth switch 114d are active, connecting the selected electrode 120 to the source follower 111 and connecting the source follower 111 to the recording channel 130. The selector 133 of the recording channel 130 may be activated to provide a bias current so as to enable read out of a pixel signal from the source follower 111.

In the configuration of FIG. 4a, the voltage sensed by the electrode 120 may be transferred to the recording channel 130. The pixel 110 may thus be set in this configuration for recording cell potentials, such as for recording an ExC AP or an InC AP.

Figure 4B:
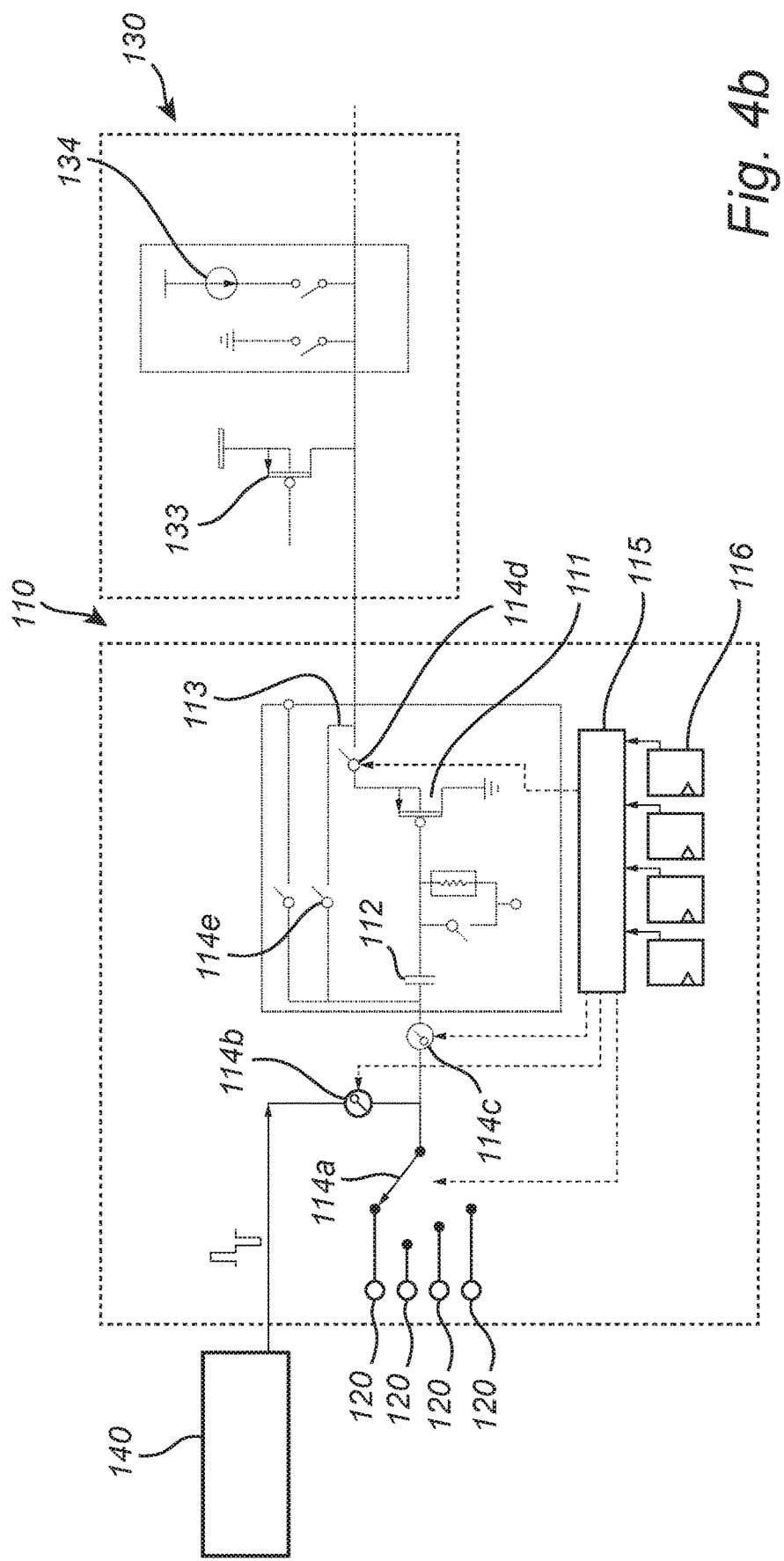

In FIG. 4b, configuration settings for the pixel 110 in a stimulation mode is illustrated. Here, the second switch 114b is active, which implies that the pixel 110 is connected to the stimulation unit 140 for receiving a stimulating signal. Further, the third switch 114c is not active, thus disconnecting the electrode 120 from the source follower 111 and from the recording channel 130. Thus, no signal is detected from the pixel 110 in this mode.

In the configuration of FIG. 4b, the pixel 110 may receive a current stimulating signal or a voltage stimulating signal. This may be used for providing CVS for controlled electrode potential to a cell or for providing CCS for controlled charge delivery to the cell. The stimulating signal may be used to influence cell behavior, which may then be studied or to induce electroporation for InC recording.

Figure 4C:
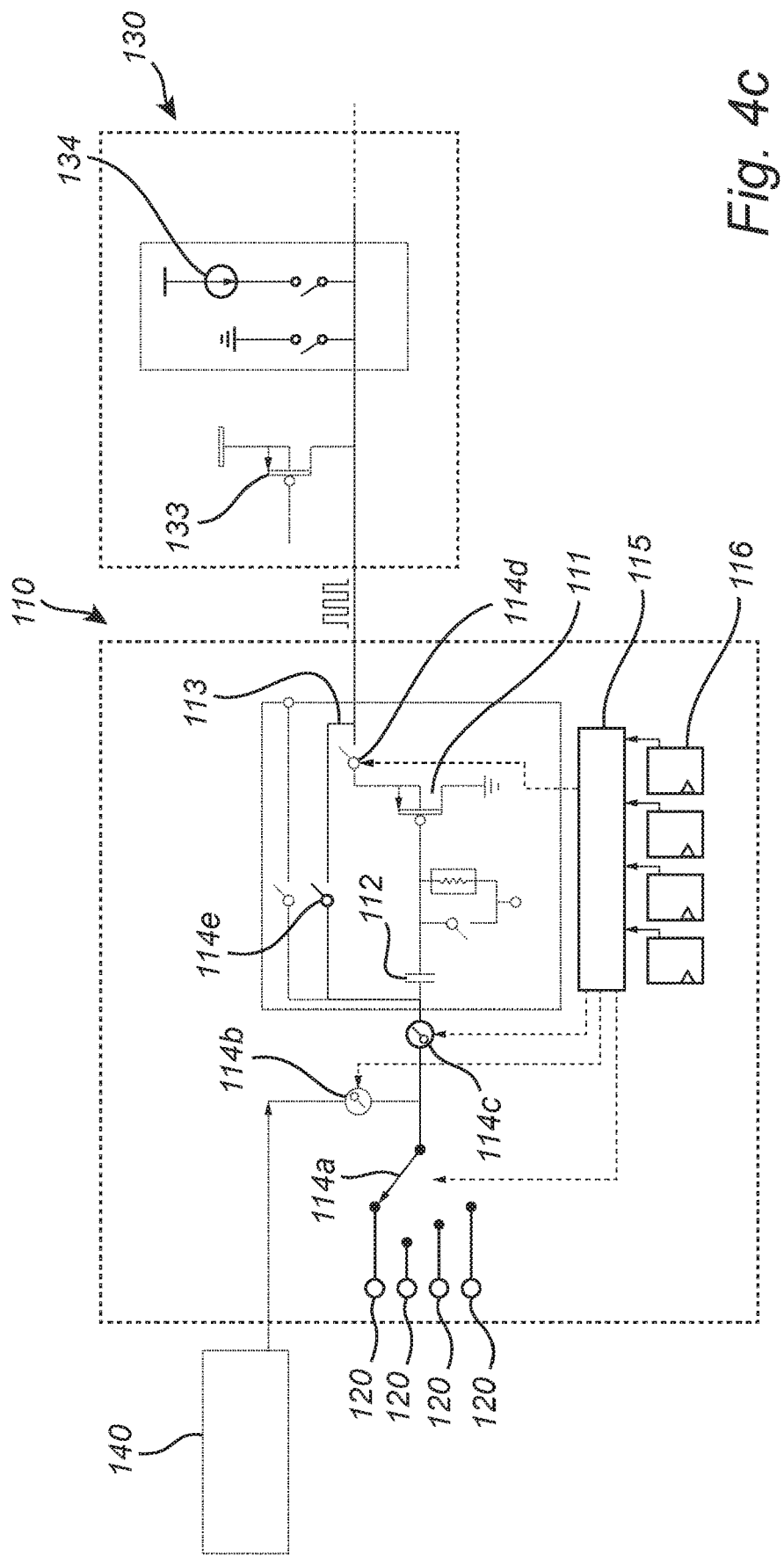

In FIG. 4c, configuration settings for the pixel 110 in an impedance monitoring mode is illustrated. Here, the second switch 114b is not active, which implies that the pixel 110 is not connected to the stimulation unit 140. Further, the third switch 114c is active for connecting the electrode 120 towards the recording channel 130. However, the fourth switch 114d is not active such that the source follower 111 is not connected to the recording channel 130. Instead, a fifth switch 114e is active for activating the direct connection 113 between the electrodes 120 and the recording channel 130 by-passing the source follower 111. Thus, the selected electrode 120 is directly connected to the recording channel 130.

The connection between the selected electrode 120 and the recording channel 130 may be used for providing a current stimulating signal from the recording channel 130 to the electrode 120, such that an induced voltage may be sensed. In the impedance monitoring mode, the current source 134 of the recording channel 130 may thus be activated to provide a stimulation signal to the electrode 120 via the direct connection 113. Further, the selector 133 may be inactive.

This configuration enables fast monitoring of an impedance of the cell. Thus, a current stimulation signal is provided from the recording channel 130 and the recording channel 130 may detect a voltage induced by the stimulation for determining of the impedance.

In FIG. 4d, configuration settings for the pixel 110 in an IS mode is illustrated. Here, the second switch 114b is active, which implies that the pixel 110 is connected to the stimulation unit 140 for receiving a stimulating signal. Further, the third switch 114c and the fourth switch 114d are active, connecting the selected electrode 120 to the source follower 111 and connecting the source follower 111 to the recording channel 130. The selector 133 of the recording channel 130 may be activated to provide a bias current so as to enable read out of a pixel signal from the source follower 111.

In the configuration of FIG. 4d, the pixel 110 may receive a current stimulating signal from the stimulation unit 140. The recording channel 130 may receive a voltage signal induced by the stimulating signal in order to enable determination of an impedance of the cell.

The stimulating signal may be swept by the stimulation unit 140, such that an impedance may be determined for a plurality of different frequencies within a range of frequencies, so as to enable IS. The frequency may for instance be swept between 10 Hz and 1 MHz.

Figure 5:
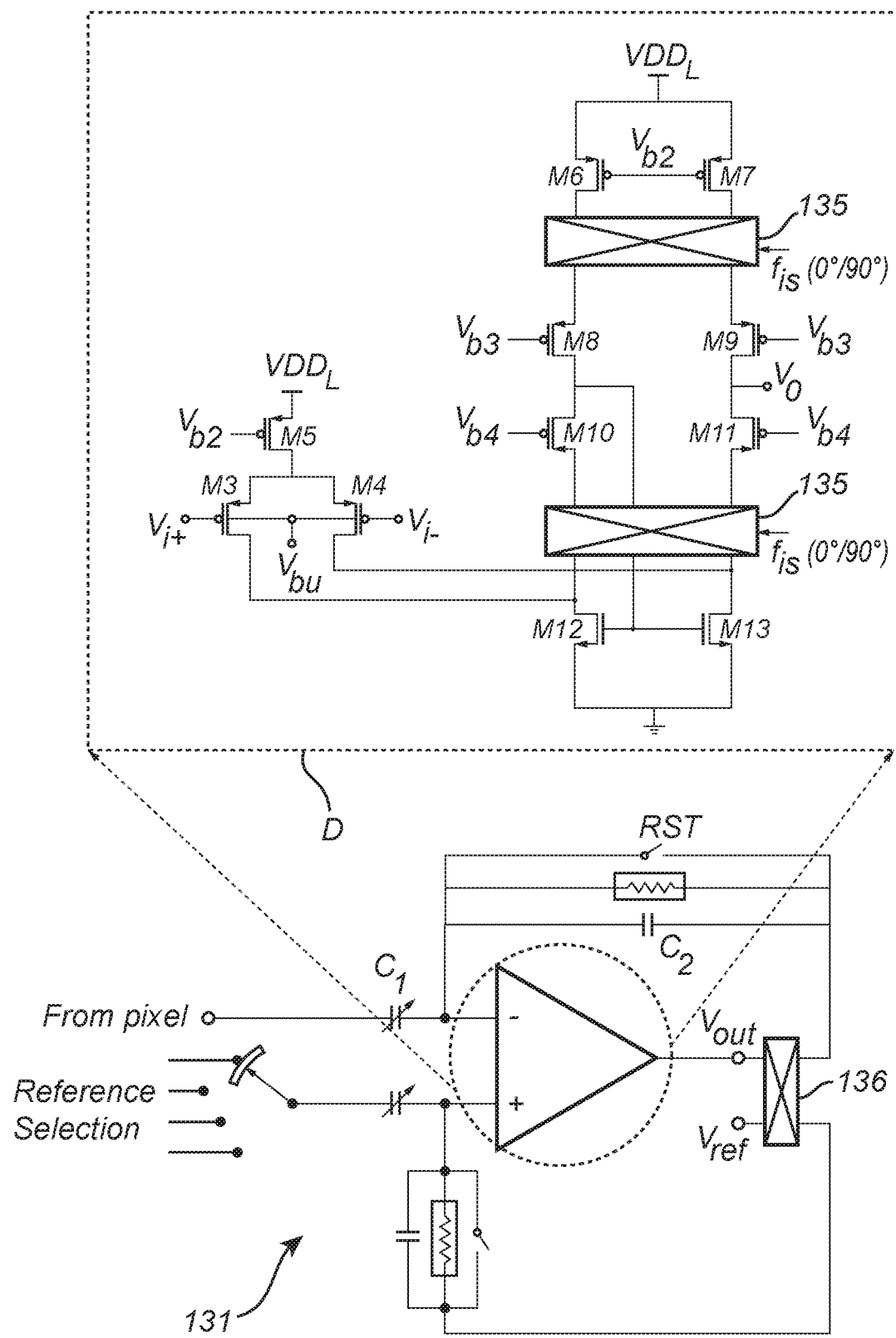
FIG. 5 is a schematic view of a reconfigurable component of a recording channel of the device.

Referring now to FIG. 5, the reconfigurable component 131 will be further described. The reconfigurable component 131 is connected to the pixel 110 for receiving a pixel signal. As discussed above, the pixel 110 may be selectively set in different configurations such that the pixel 110 may be disconnected from the recording channel 130, in which case the reconfigurable component 131 will not receive any pixel signal, or for providing different types of pixel signals.

The reconfigurable component 131 may comprise an operational transconductance amplifier (OTA), which receives the pixel signal and a reference signal and provides a differential amplification of these signals. The recording channel 130 may be configured to select a reference electrode, which may be arranged in the active sensor area 104 and may provide a reference voltage to which the pixel signal may be compared.

As illustrated in magnification D in FIG. 5, the OTA may comprise transistors M3-M4 forming an input differential pair of the OTA and being connected to receive the pixel signal and the reference signal, respectively. Further, the OTA may be configured as a folded cascode OTA, wherein transistors M6-M7 and M12-M13 are current mirrors and define the current employed in the OTA and M8-M11 are cascode devices used to increase the output impedance of the OTA.

The OTA may further comprise modulating elements or choppers 135, which are connected between the current mirrors and the cascode devices in the OTA. The modulating elements 135 may be selectively enabled or disabled for affecting a functionality of the OTA.

The reconfigurable component 131 may thus be set into a first mode, wherein the modulating elements 135 are disabled and the reconfigurable component 131 functions as a differential amplifier for amplifying the difference between the pixel signal and the reference signal.

The reconfigurable component 131 may further be set into a second mode, wherein the modulating elements 135 in the OTA are enabled. Further, a modulating element 136 providing a modulation of the signal output by the OTA and fed back to the OTA via a feedback loop and a modulation of the reference signal may be selectively enabled in the second mode. The reconfigurable component 131 may in the second mode be configured to receive a signal synchronized with a stimulating signal, such that the reconfigurable component 131 may be configured to downconvert a received pixel signal to baseband and upmodulate signals relating to ExC and/or InC APs for filtering out these signals.

The gain provided by the OTA may be controlled by programming variable capacitors at the input of the OTA. The gain is formed by a capacitor ratio between C1 and C2.

Figure 6A:
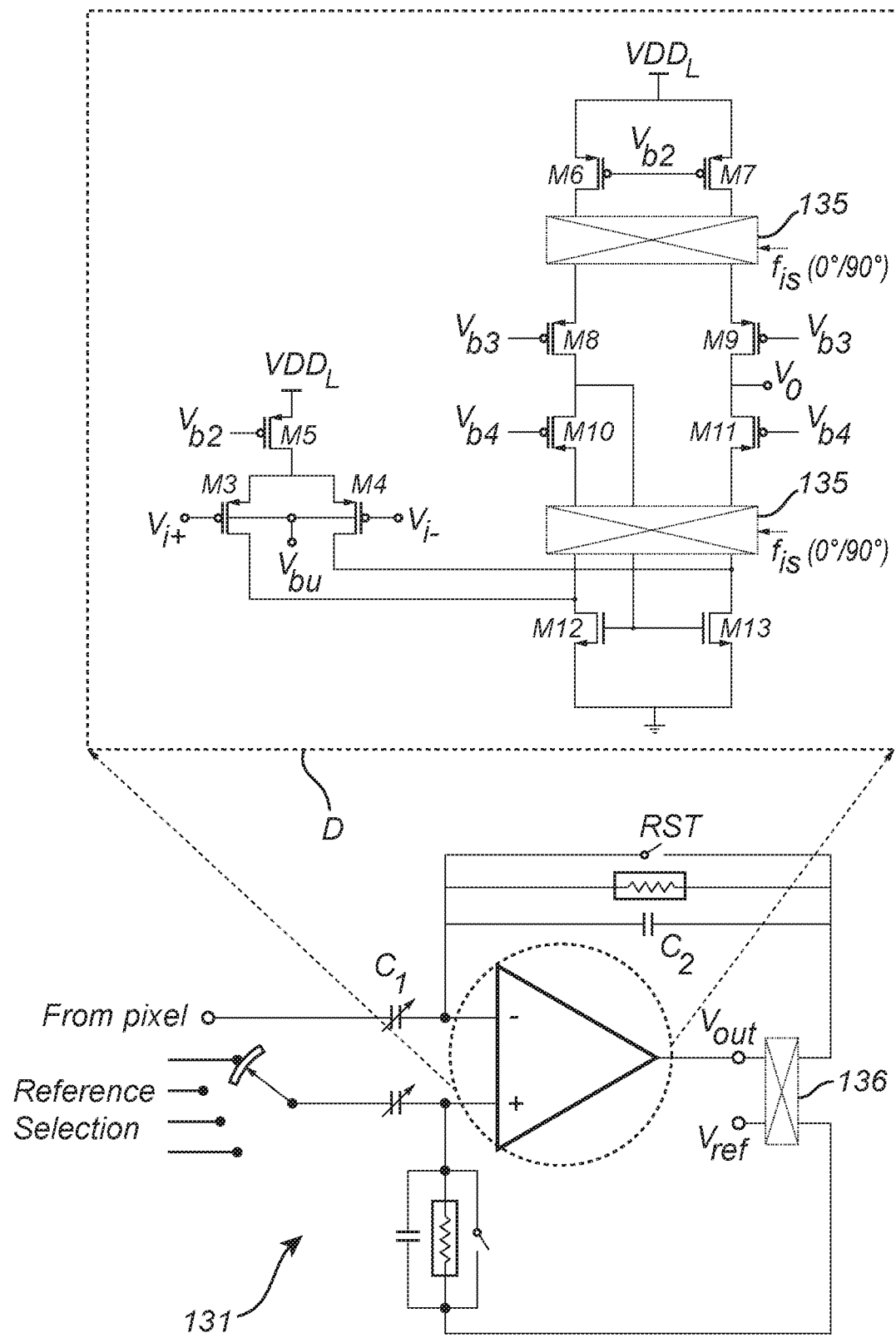
FIGS. 6a-c are schematic views illustrating different configurations of the reconfigurable component.
Figure 6B:
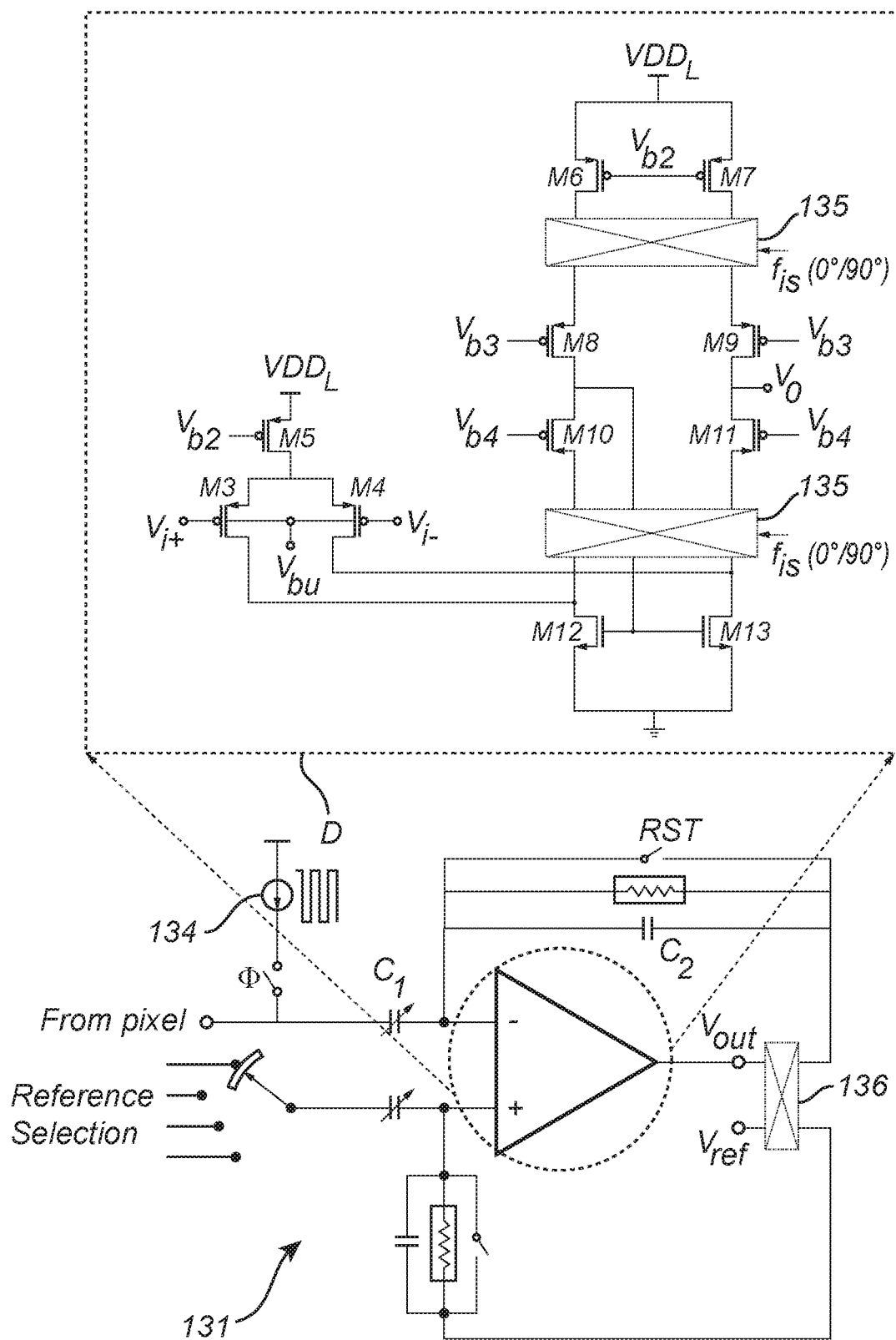
Figure 6C:
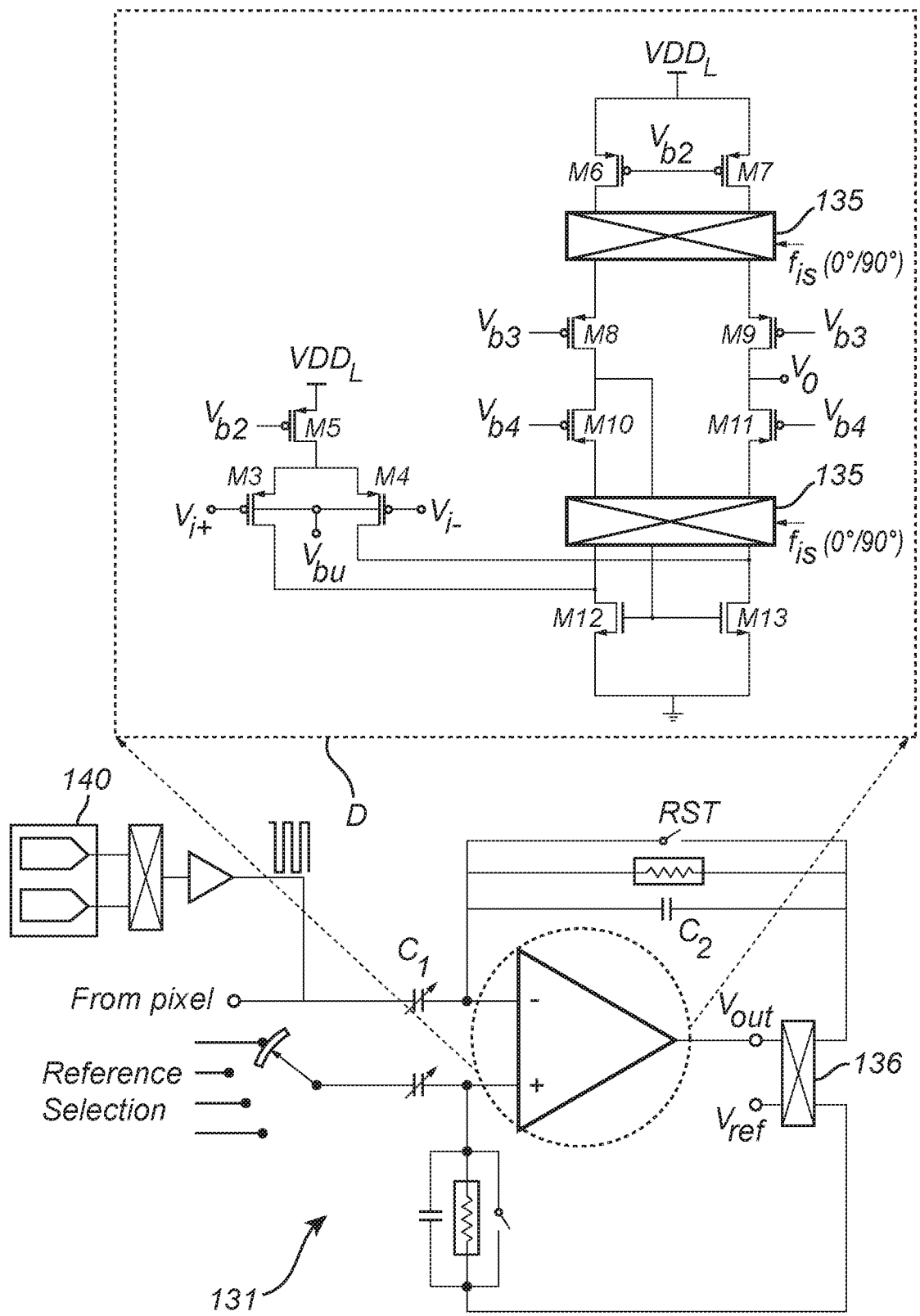

Referring now to FIGS. 6a-c, different configurations of the reconfigurable component 131 will be described.

In FIG. 6a, configuration settings for the reconfigurable component 131 in a recording mode is illustrated. Here, the modulating elements 135, 136 are disabled and the OTA functions as a differential amplifier receiving a voltage signal from the pixel 110 and a reference signal.

The reconfigurable component 131 may be used in this mode when an InC AP or an ExC AP is to be detected. The gain of the reconfigurable component 131 may be varied depending on the measurement modality. Thus, for measuring an ExC AP, a relatively high gain of the reconfigurable component 131 may be set, via control of the capacitor C1, whereas, for measuring an InC AP, a relatively low gain of the reconfigurable component 131 may be set. A lower gain may be used when the InC AP is measured as the input signal typically has a larger amplitude for InC AP compared to ExC AP.

Further, the signal conditioning unit 132 may also be controlled in dependence of the measurement to be made. For instance, for measuring the ExC AP, the signal conditioning unit 132 may be set to filter low frequency components with a high-pass filter, whereas such a high-pass filter may be disabled for measuring the InC AP as low frequencies are relevant for InC AP.

Also, the signal conditioning unit 132 may provide further gain tuning of the signal by control of the programmable gain amplifier (PGA).

In FIG. 6b, configuration settings for the reconfigurable component 131 in an impedance monitoring mode is illustrated. As for the recording mode, the modulating elements 135, 136 are disabled and the OTA functions as a differential amplifier receiving a voltage signal from the pixel 110 and a reference signal.

In this case, the current source 134 of the recording channel 130 is activated to provide a stimulation signal to the electrode 120 with a pre-set frequency. The pixel signal received by the reconfigurable component 131 may thus be modulated by the frequency provided by the current source 134 such that lower frequency signals relating to InC AP or ExC AP will be removed.

The reconfigurable component 131 may thus be used in this mode when impedance monitoring using the pre-set frequency of the current source 134 is to be performed. In this measurement modality, the gain of the reconfigurable component 131 may be set to be even lower than a gain used for measuring an InC AP in order to avoid saturation of the OTA.

In FIG. 6c, configuration settings for the reconfigurable component 131 in an IS measurement mode is illustrated. Here, the modulating elements 135, 136 are enabled and the modulating elements 135, 136 of the reconfigurable component 131 are synchronized to the stimulating signal to downconvert a received pixel signal to baseband and upmodulate signals relating to ExC and/or InC APs for filtering out these signals. The phase of the modulating elements 135, 136 is programmable allowing to extract real and imaginary part of the cell impedance in an interleaved manner.

Figure 7:
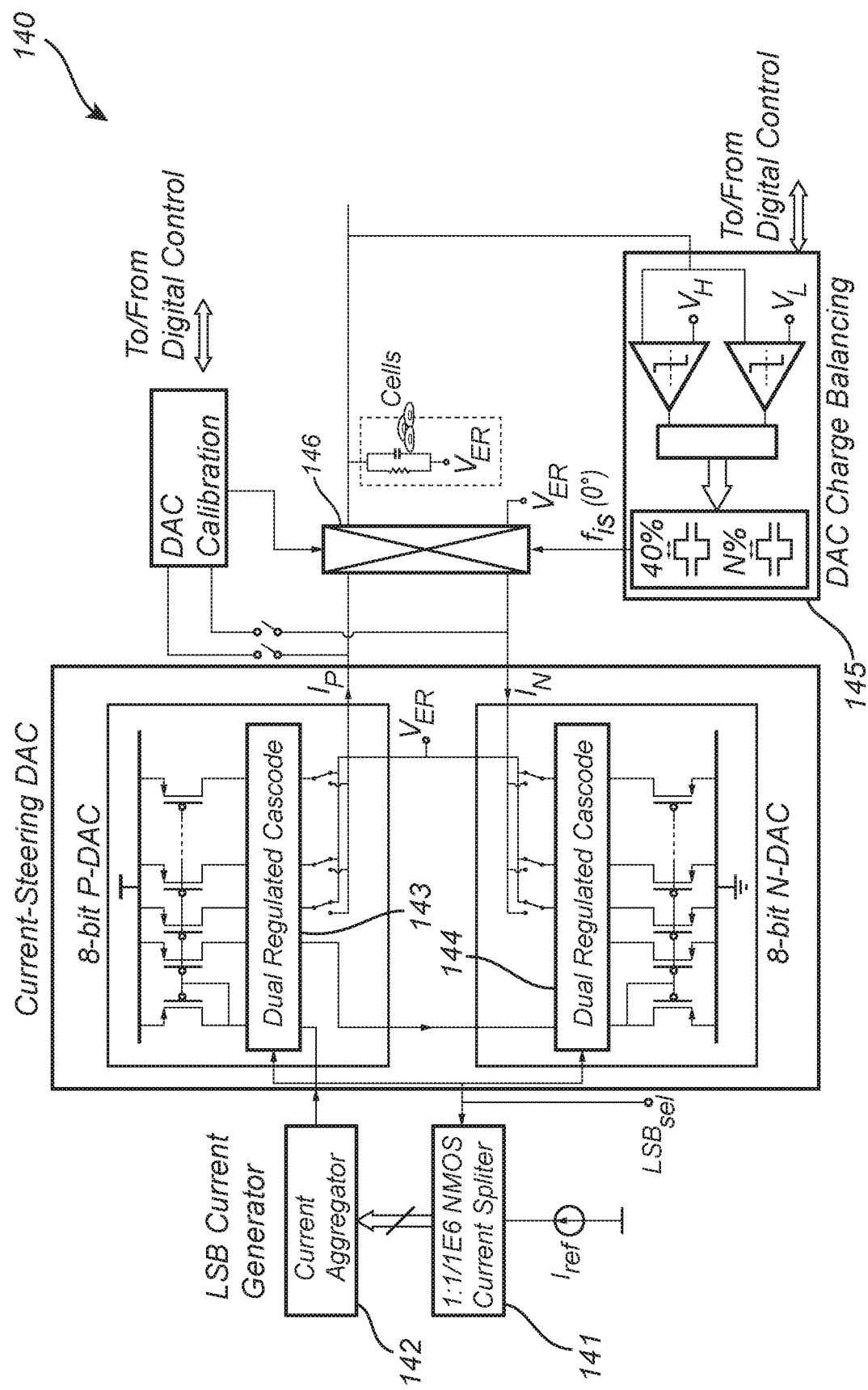
FIG. 7 is a schematic view of a stimulation unit of the device.

Referring now to FIG. 7, a stimulation unit 140 will be further described.

Each stimulation unit 140 may be independently controlled for such that pixels 110 connected to different stimulation units 140 may receive different stimulation signals.

The stimulation unit may have a voltage digital-to-analog converter (VDAC) and a current digital-to-analog converter (IDAC), which may be configured to convert a digital input to a voltage signal and a current signal, respectively.

The VDAC may be formed as a binary R-2R resistor ladder, buffered by an amplifier and able to drive a load of a plurality of parallel electrodes during CVS.

The IDAC may be used for two different purposes. Firstly, the IDAC may be used to deliver arbitrary current waveforms during CCS. Secondly, the IDAC may be used to provide a DC current during IS. Since the impedance to be measured during IS can range from tens of GΩ to hundreds of kΩ (5 orders of magnitude), the IDAC may advantageously be able to generate currents from few pA to hundreds of nA. To achieve this, the IDAC is designed using a binary current-steering architecture with independent source and sink outputs, as illustrated in FIG. 7.

Two possible LSB current references (2 pA or 500 pA) are generated by combining a current splitter 141 based on a R-2R principle, and a current aggregator 142. Dual regulated cascodes 143, 144 (for the 2 ranges) are used to ensure a high output impedance (>100 GΩ).

A digital-assisted closed-loop charge-balancing (CB) circuit 145 in each stimulation unit 140 may prevent residual charge injection into electrode-cell interface. For this, positive or negative pulses of the stimulation signal are extended based on crossing of predefined electrode voltage thresholds, as sensed by the CB circuit 145 being connected to receive the electrode voltage as input.

In IS mode, the stimulation units 140 generate currents of varied frequency and amplitude. For IS mode, the device 100 may use a square-wave current modulation, provided by a chopper 146 after the IDAC, so as to provide a square-wave instead of sine waves. This may ensure that the stimulation unit 140 may be operated with low power requirements and may be implemented in a small integrated circuit area.

In the above the inventive concept has mainly been described with reference to a limited number of examples. However, as is readily appreciated by a person skilled in the art, other examples than the ones disclosed above are equally possible within the scope of the inventive concept, as defined by the appended claims.

The invention claimed is:

1. A device for analysis of cells, said device comprising:
an active sensor area presenting a surface for cell growth on the device;
a microelectrode array comprising a plurality of pixels in the active sensor area,
wherein each pixel comprises at least one electrode at the surface,
wherein the at least one electrode is configured to form contact with cells for providing stimulating signals to cells and/or measuring electrical signals from cells,
wherein each pixel further comprises pixel circuitry comprising at least one switch for setting a configuration of the pixel circuitry and wherein each pixel is configured to individually receive a control signal for controlling the configuration of the pixel circuitry and set a measurement modality of the pixel; and
recording circuitry having a plurality of recording channels,
wherein each pixel is connected to a recording channel, the recording channel being configured to receive signals from the pixels in the active sensor area,
wherein each recording channel of the recording circuitry comprises a reconfigurable component, which is selectively configurable between a first mode, in which the reconfigurable component is configured to amplify a received pixel signal, and a second mode, in which the reconfigurable component is configured to selectively pass a frequency band of the received pixel signal,
wherein the reconfigurable component comprises an operational transconductance amplifier (OTA) having modulating elements, wherein the OTA is configured to disable the modulating elements in the first mode such that the OTA is configured to amplify the received pixel signal, wherein the OTA is configured to enable the modulating elements in the second mode such that the OTA is configured to selectively pass the frequency band of the received pixel signal, and wherein each pixel is selectively configurable between a first configuration in which the pixel is connected to the recording channel such that the reconfigurable component receives the signal from the pixel and a second configuration in which the pixel is disconnected from the recording channel such that the reconfigurable component does not receive any signal from the pixel.

2. The device according to claim 1, wherein each reconfigurable component in the second mode is configured to receive a modulation signal which is synchronized with an input current for stimulating cells on the active sensor area, wherein each reconfigurable component is configured to modulate the received pixel signal with the modulation signal for down conversion of the received pixel signal to baseband.

3. The device according to claim 1, wherein each reconfigurable component in the first mode is configured to inactivate a modulating element and to amplify the received pixel signal.

4. The device according to claim 1, wherein each pixel is configured to be set to a recording mode, wherein a signal from the at least one electrode is connected to a source follower, which is further connected to a recording channel of the recording circuitry for providing a pixel signal to the recording channel.

5. The device according to claim 1, wherein each pixel is configured to be set to a stimulation mode, wherein the at least one electrode is connected to receive a stimulating signal.

6. The device according to claim 5, wherein each pixel is configured to be set to the stimulation mode followed by a recording mode, wherein a signal from the at least one electrode is connected to a source follower, which is further connected to a recording channel of the recording circuitry for providing a pixel signal to the recording channel, such that the signal detected by the at least one electrode in the recording mode corresponds to an intracellular action potential.

7. The device according to claim 1, wherein each pixel comprises a plurality of electrodes and each pixel is configured to be set to an impedance measurement mode, wherein at least a first electrode is configured to be connected to receive a stimulating signal and at least a second electrode is configured to be connected to a source follower, which is further connected to a recording channel of the recording circuitry for providing a pixel signal to the recording channel.

8. The device according to claim 7, wherein the recording channel comprises a current source, which is configured to provide a current with a fixed, pre-set frequency, and wherein the pixel in the impedance measurement mode is configured to be connected to receive a signal from the current source for receiving the stimulating signal.

9. The device according to claim 7, further comprising a stimulation unit for controlling generation of the stimulating signal, wherein the pixel in the impedance measurement mode is configured to be connected to the stimulation unit for receiving the stimulating signal, wherein the stimulation unit is configured to sweep a frequency of the stimulating signal for performing impedance spectroscopy measurements.

10. The device according to claim 9, wherein the stimulation unit comprises a current-steering architecture with independent source and sink outputs for generating output of two different current levels.

11. The device according to claim 9, wherein the stimulation unit comprises a charge balancing unit for preventing residual charge injection from electrode to cell.

12. The device according to claim 1, further comprising a digital control unit being configured to provide control signals for controlling configuration of each pixel and of each reconfigurable component.

13. The device according to claim 1, wherein each recording channel further comprises a signal conditioning unit, which is configured to a signal from the reconfigurable component of the respective recording channel and process the signal.

14. The device according to claim 1, wherein each reconfigurable component is configured based upon the measurement modality of the pixel corresponding to the respective reconfigurable component.

15. A method for analysis of cells which are arranged on an active sensor area of a microelectrode array comprising a plurality of pixels, wherein each pixel comprises at least one electrode forming contact with a cell and each pixel is connected to a recording channel, the recording channel being configured to receive signals from the pixels and having a reconfigurable component, and wherein each pixel further comprises pixel circuitry comprising at least one switch for setting a configuration of the pixel circuitry and wherein each pixel is configured to individually receive a control signal for controlling the configuration of the pixel circuitry and set a measurement modality of the pixel, said method comprising:

providing a pixel control signal for setting the configuration of the pixel circuitry to select a measurement modality of the pixel;

providing a recording channel control signal for setting a configuration of the reconfigurable component to select between a first mode and a second mode of processing a received signal from the pixel, wherein in the first mode the reconfigurable component is configured to amplify a received pixel signal, and in the second mode the reconfigurable component is configured to selectively pass a frequency band of the received pixel signal, wherein the reconfigurable component comprises an operational transconductance amplifier (OTA) having modulating elements, wherein the OTA is configured to disable the modulating elements in the first mode such that the OTA is configured to amplify the received pixel signal, wherein the OTA is configured to enable the modulating elements in the second mode such that the OTA is configured to selectively pass the frequency band of the received pixel signal, and wherein each pixel is selectively configurable between a first configuration in which the pixel is connected to the recording channel such that the reconfigurable component receives the signal from the pixel and a second configuration in which the pixel is disconnected from the recording channel such that the reconfigurable component does not receive any signal from the pixel;

acquiring a measurement signal by the pixel based on the selected measurement modality and transferring a pixel signal to the recording channel; and processing the received pixel signal by the recording channel based on the selected mode of processing.

16. The method according to claim 15, wherein the configuration of the reconfigurable component is selected based upon the measurement modality of the pixel corresponding to the respective reconfigurable component.

\* \* \* \* \*